US008283486B2

(12) United States Patent
Tsuchida

(10) Patent No.: US 8,283,486 B2
(45) Date of Patent: Oct. 9, 2012

(54) NORBORNANE SKELETON STRUCTURE-CONTAINING ORGANOSILICON COMPOUND AND METHOD OF PRODUCING SAME

(75) Inventor: Kazuhiro Tsuchida, Takasaki (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 13/160,127

(22) Filed: Jun. 14, 2011

(65) Prior Publication Data

US 2011/0245525 A1 Oct. 6, 2011

Related U.S. Application Data

(62) Division of application No. 12/265,802, filed on Nov. 6, 2008, now Pat. No. 8,034,965.

(30) Foreign Application Priority Data

Nov. 9, 2007 (JP) .................................. 2007-292579
Nov. 16, 2007 (JP) .................................. 2007-298494

(51) Int. Cl.
   C07F 7/18 (2006.01)
   C07F 7/12 (2006.01)
(52) U.S. Cl. ......................... 556/441; 556/482; 556/488
(58) Field of Classification Search .................... None
   See application file for complete search history.

(56) References Cited

U.S. PATENT DOCUMENTS

| 3,737,334 | A | 6/1973 | Doran et al. |
| 4,642,356 | A | 2/1987 | Langner et al. |
| 4,921,976 | A | 5/1990 | Kabeta |
| 4,957,989 | A | 9/1990 | Saitoh |
| 2004/0161698 | A1 | 8/2004 | Kanagasabapathy et al. |
| 2007/0218402 | A1 | 9/2007 | Kinsho et al. |
| 2008/0026314 | A1 | 1/2008 | Nishimura et al. |

FOREIGN PATENT DOCUMENTS

| EP | 0 203 519 A1 | 12/1986 |
| JP | 61-15887 | 1/1986 |
| JP | 1-132591 | 5/1989 |
| JP | 11-501631 | 2/1999 |
| JP | 2002-88089 | 3/2002 |
| JP | 2005-29742 | 2/2005 |
| JP | 2005-120012 | 5/2005 |
| JP | 2005-139169 | 6/2005 |
| WO | WO 96/27599 | 9/1996 |
| WO | WO 03/074448 A2 | 9/2003 |

OTHER PUBLICATIONS

Crivello et al., Preparation of 1-Propenyl Ether Functional Siloxanes by Chemoselective Hydrosilation and Their Cationic Photopolymerization, Macromolecules, 1995, vol. 28, No. 24, pp. 8057-8064.*
Computer generated English translation of JP 2002-088089, published Mar. 2002.*
Zavin, B. G., et al., "Preparation of organosilanes and oligoorganosiloxanes by the hydrosilylation reaction of halomethyl derivatives of bicyclo [2.2.1]hept-5-ene", retrieved from STN Database accession No. 1996: 488154, RN 182067-21-6, XP002554567, 3 Pages.
Mamedov, M. A., et al., "Effect of the nature of the halogen atom on the addition reaction of silicon hydrides to halogen-containing unsaturated bicyclic compounds", retrieved from STN Database accession No. 1967:65563 RN 29861-94-7, RN 29861-95-8, RN 29861-96-9, RN 29861-98-1, RN 29862-01-9, XP002554568, 4 Pages.
Akhmedov, I. M., et al., "Addition of silanes to chlorine-containing bicyclic hydrocarbons", retrieved from STN Database accession No. 1965:3184 RN 29861-95-8, RN 95027-41-1, RN 95062-46-9, XP002554569, 2 Pages.
L. Lecamp, et al., "Polydiméthyl Siloxane Photoréticulable Par Voie Cationique-I. Synthèse Et Photoréticulation De Polydiméthyl Siloxane A Greffons Epoxy Norbornène", European Polymer Journal, vol. 33, No. 9, Sep. 1997. pp. 1453-1462 (With English Abstract).
Azerbaidzhanskii Khimicheskii Zhurnal, (2), 1965. pp. 46-50.
Zhurnal Obshchei Khimii, 36 (11), 1966. pp. 2018-2022.
Azerbaidzhanskii Khimicheskii Zhurnal, (2), 1968. pp. 105-108.
Office Action issued Dec. 22, 2011 in Europe Application No. 08 253 651.7.
Barry Arkles, et al., "Silane Coupling Agents: Connecting Across Boundaries", in Barry Arkles: "Silicon Compounds: Silanes and Silicones", Jan. 1, 2004, pp. 165-172.

* cited by examiner

*Primary Examiner* — Rosalynd Keys
(74) *Attorney, Agent, or Firm* — Oblon, Spivak, McClelland, Maier & Neustadt, L.L.P.

(57) ABSTRACT

Disclosed are a radiation-polymerizable functional group-containing organosilicon compound, including (A) a norbornane skeleton structure, (B) a hydrolyzable silyl group bonded directly to the norbornane skeleton structure, and (C) a radiation-polymerizable functional group bonded to the norbornane skeleton structure, either directly or via a carbon atom, a hetero atom, or a combination thereof, and a method of producing the radiation-polymerizable functional group-containing organosilicon compound. Also disclosed are a haloalkyl group-containing organosilicon compound, including (D) a norbornane skeleton structure, (E) a hydrolyzable silyl group bonded directly to the norbornane skeleton structure, and (F) a haloalkyl group, which is bonded directly to the norbornane skeleton structure and either contains or does not contain a hetero atom, and a method of producing the haloalkyl group-containing organosilicon compound. These organosilicon compounds are useful as silane coupling agents having superior heat resistance stability.

4 Claims, 10 Drawing Sheets

NORBORNANE SKELETON STRUCTURE-CONTAINING ORGANOSILICON COMPOUND AND METHOD OF PRODUCING SAME

CROSS REFERENCE TO RELATED APPLICATIONS

This application is a divisional of U.S. patent application Ser. No. 12/265,802, filed Nov. 6, 2008 the disclosures of which are incorporated herein by reference in their entireties. This application claims priority to Japanese Patent Application JP2007-292579, filed Nov. 9, 2007 and Japanese Patent Application JP2007-298494, filed Nov. 16, 2007, the disclosures of which are incorporated herein by reference in their entireties.

BACKGROUND OF THE INVENTION

1. Field of the Invention

The present invention relates to a novel organosilicon compound comprising a radiation-polymerizable functional group or a haloalkyl group, a norbornane skeleton structure, and a hydrolyzable silyl group, as well as a method of producing such an organosilicon compound.

2. Description of the Prior Art

Organosilicon compounds having a hydrolyzable silyl group generally generate a silanol group in the presence of water, and this silanol group is able to react with a hydroxyl group on the surface of an inorganic material, meaning the organosilicon compound can be used for surface treatment of the inorganic material. Furthermore, organosilicon compounds of this type that also comprise an organic functional group that reacts with organic resins are widely used as silane coupling agents, organic and inorganic resin modifiers, adhesion assistants and additives, and the use and application of such compounds is well known, with numerous patent applications having been filed.

In a typical silane coupling agent, the hydrolyzable silyl group site that reacts with inorganic materials and the organic functional group site that reacts with organic resins are almost always linked via a linear hydrocarbon chain. However, the treated item obtained by conducting treatment with the silane coupling agent is frequently used under high-temperature conditions, and the low heat resistance of the linear hydrocarbon chain under such conditions often creates problems.

Against this background, a norbornane skeleton structure, which is a polycyclic hydrocarbon skeleton structure, is a three dimensionally rigid structure, and it is known that incorporating this skeleton structure into the structure of an organic polymer increases the heat resistance of the polymer.

In conventional silane coupling agents, the incorporation of a functional group such as an acryloyl group, methacryloyl group, epoxy group, amino group or mercapto group as an organic group that reacts with organic resins is well known, and such silane coupling agents are used in all manner of applications.

SUMMARY OF THE INVENTION

The present invention has been developed in light of the above circumstances, and has an object of providing a novel organosilicon compound in which a norbornane skeleton structure that contributes to heat resistance stability is incorporated into the linking region between a hydrolyzable silyl group and a radiation-polymerizable functional group or a haloalkyl group that functions as an organic functional group, as well as providing a method of producing the organosilicon compound.

As a result of intensive investigation aimed at achieving the above object, the inventors of the present invention developed an organosilicon compound in which a hydrolyzable silyl group and either a radiation-polymerizable functional group or a haloalkyl group are linked via a norbornane skeleton structure. The inventors also developed a method of producing such a compound, and they were thus able to complete the present invention.

In other words, a first aspect of the present invention provides a radiation-polymerizable functional group-containing organosilicon compound, comprising:
(A) a norbornane skeleton structure,
(B) a hydrolyzable silyl group bonded directly to the norbornane skeleton structure, and
(C) a radiation-polymerizable functional group bonded to the norbornane skeleton structure, either directly or via a carbon atom, a hetero atom, or a combination thereof.

A second aspect of the present invention provides a method of producing a radiation-polymerizable functional group-containing organosilicon compound comprising
(A) a norbornane skeleton structure,
(B) a hydrolyzable silyl group bonded directly to the norbornane skeleton structure, and
(C) a radiation-polymerizable functional group bonded to the norbornane skeleton structure, either directly or via a carbon atom, a hetero atom, or a combination thereof,
the method comprising:
reacting a haloalkyl group-containing organosilicon compound, comprising
(D) a norbornane skeleton structure,
(E) a hydrolyzable silyl group bonded directly to the norbornane skeleton structure, and
(F) a haloalkyl group, which is bonded directly to the norbornane skeleton structure, and either contains or does not contain a hetero atom, with
at least one salt having a radiation-polymerizable functional group, selected from the group consisting of alkali metal salts of organic acids having a radiation-polymerizable functional group and alkaline earth metal salts of organic acids having a radiation-polymerizable functional group,
at a temperature within a range from 50 to 150° C.

A third aspect of the present invention provides a haloalkyl group-containing organosilicon compound, comprising:
(D) a norbornane skeleton structure,
(E) a hydrolyzable silyl group bonded directly to the norbornane skeleton structure, and
(F) a haloalkyl group, which is bonded directly to the norbornane skeleton structure, and either contains or does not contain a hetero atom.

A fourth aspect of the present invention provides a method of producing a haloalkyl group-containing organosilicon compound comprising
(D) a norbornane skeleton structure,
(E) a hydrolyzable silyl group bonded directly to the norbornane skeleton structure, and
(F) a haloalkyl group, which is bonded directly to the norbornane skeleton structure, and either contains or does not contain a hetero atom, the method comprising:
subjecting a hydrolyzable silane having a hydrogen atom bonded directly to a silicon atom, and a norbornene derivative having a norbornene skeleton structure and a haloalkyl group that is bonded directly to the norbornene skeleton structure and either contains or does not contain a hetero atom, to a hydrosilylation reaction in the presence of a catalyst.

Because the radiation-polymerizable functional group-containing organosilicon compound of the present invention includes a rigid polycyclic hydrocarbon skeleton structure, namely a norbornane skeleton structure, as the unit that links the hydrolyzable silyl group and the radiation-polymerizable functional group, the organosilicon compound exhibits superior heat resistance stability to conventional compounds containing a linear hydrocarbon chain as this linking unit. Furthermore, the radiation-polymerizable functional group-containing organosilicon compound of the present invention contains a radiation-polymerizable functional group that functions as an organic functional group having superior reactivity with organic resins. Accordingly, the radiation-polymerizable functional group-containing organosilicon compound of the present invention is useful as a silane coupling agent having improved heat resistance stability.

Similarly, because the haloalkyl group-containing organosilicon compound of the present invention also includes a rigid polycyclic hydrocarbon skeleton structure, namely a norbornane skeleton structure, as the unit that links the hydrolyzable silyl group and the haloalkyl group, this organosilicon compound also exhibits superior heat resistance stability to conventional compounds containing a linear hydrocarbon chain as this linking unit. Accordingly, the haloalkyl group-containing organosilicon compound of the present invention is itself useful as a silane coupling agent having improved heat resistance stability. Moreover, because all manner of organic functional groups can be introduced at the haloalkyl group of the haloalkyl group-containing organosilicon compound of the present invention, this organosilicon compound is also useful as a precursor to a multitude of silane coupling agents having excellent heat resistance stability.

DETAILED DESCRIPTION OF THE PREFERRED EMBODIMENTS

Figure 1:
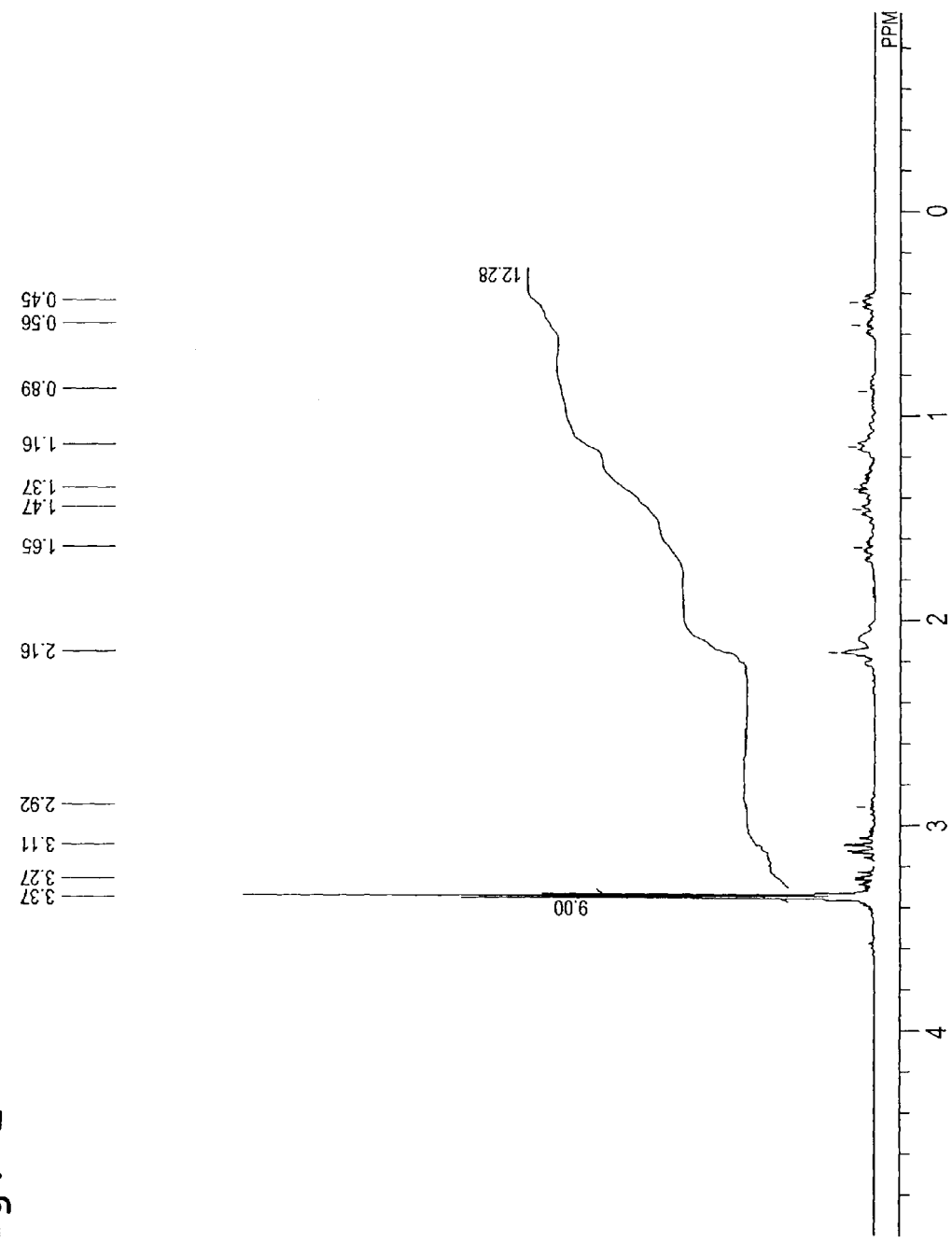
FIG. 1 is a diagram showing the $^1$H NMR spectrum of the reaction product of an example 1.

A more detailed description of the present invention is provided below.
[Radiation-Polymerizable Functional Group-Containing Organosilicon Compound]
A radiation-polymerizable functional group-containing organosilicon compound of the present invention comprises:
(A) a norbornane skeleton structure,
(B) a hydrolyzable silyl group bonded directly to the norbornane skeleton structure, and
(C) a radiation-polymerizable functional group bonded to the norbornane skeleton structure, either directly or via a carbon atom, a hetero atom, or a combination thereof.

<(A) Norbornane Skeleton Structure>
The structure (A) is a norbornane skeleton structure. In this description, a "norbornane skeleton structure" refers to an atom grouping that remains when 2 to 12 hydrogen atoms are removed from norbornane, and provided this definition is satisfied, there are no limitations on the number of hydrogen atoms removed or the positions of those hydrogen atoms.

Examples of this norbornane skeleton structure of the structure (A) include norbornylene groups represented by a structural formula shown below:

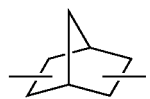

namely, divalent hydrocarbon groups generated by removing the hydrogen atoms from position 2 or 3, and position 5 or 6 of norbornane.

<(B) Hydrolyzable Silyl Group>
The structure (B) is a hydrolyzable silyl group that is bonded directly to the norbornane skeleton structure of the structure (A). In this description, there are no particular limitations on the hydrolyzable silyl group, provided it is a silyl group that contains at least one of a monovalent hydrolyzable atom bonded directly to the silicon atom (an atom that generates a silanol group upon reaction with water) and a monovalent hydrolyzable group bonded directly to the silicon atom (a group that generates a silanol group upon reaction with water). This type of hydrolyzable silyl group generates a silanol group upon hydrolysis, and this silanol group undergoes a dehydration-condensation with an inorganic material, forming a chemical bond represented by a formula: Si—O-M (wherein, M represents the inorganic material). The radiation-polymerizable functional group-containing organosilicon compound of the present invention may include either a single hydrolyzable silyl group of the structure (B), or two or more such hydrolyzable silyl groups, and if two or more hydrolyzable silyl groups exist, these groups may be either the same or different.

Examples of the hydrolyzable silyl group of the structure (B) include silyl groups represented by a general formula (1') shown below, as well as a chlorosilyl group, bromosilyl group, methoxysilyl group, ethoxysilyl group, propoxysilyl group, butoxysilyl group or phenoxysilyl group.

<(C) Radiation-Polymerizable Functional Group>
The structure (C) is a radiation-polymerizable functional group bonded to the norbornane skeleton structure of the structure (A), either directly or via a carbon atom, a hetero atom, or a combination thereof. Upon irradiation, the radiation-polymerizable functional group of the structure (C) reacts or copolymerizes with an organic resin to form a bond. The radiation-polymerizable functional group-containing organosilicon compound of the present invention may include either a single radiation-polymerizable functional group of the structure (C), or two or more such radiation-polymerizable functional groups, and if two or more radiation-polymerizable functional groups exist, the groups may be either the same or different. In this description, in those cases where the radiation-polymerizable functional group of the structure (C) is bonded to the norbornane skeleton structure of the structure (A) via a carbon atom, a hetero atom or a combination thereof, the term "linking group" is used to describe the structure that links the structures (A) and (C).

In this description, "radiation" includes electromagnetic radiation such as microwaves, infrared radiation, ultraviolet (UV) radiation, X-rays and γ-rays, as well as particle beams such as α-beams, proton beams, electron beams and neutron beams.

Examples of the radiation-polymerizable functional group include an acryloyl group, methacryloyl group, styryl group or vinyl group, and of these, an acryloyl group or methacryloyl group or the like is preferred.

Examples of the hetero atom include an oxygen atom, sulfur atom or nitrogen atom. In those cases where the linking group includes a hetero atom, the linking group may include either a single hetero atom or two or more hetero atoms, and in the case of two or more hetero atoms, these atoms may be either the same or different. The hetero atom exists within a structure such as a carbonyl group (—C(=O)—), oxy group (—O—), thio group (—S—), imino group (—NH—) or nitro group (—N<).

Specific examples of the linking group include divalent groups such as alkylene groups that either contain or do not contain a hetero atom, a carbonyl group, an oxy group, a thio group, an imino group, or combinations thereof.

Examples of the combination of the radiation-polymerizable functional group of the structure (C) and the linking group include monovalent groups represented by a general formula (1″) shown below.

<Other Structures>

The radiation-polymerizable functional group-containing organosilicon compound of the present invention may also include other structures besides the structures (A) to (C), provided the inclusion of these other structures does not impair the object of the present invention. If such other structures are included, then the radiation-polymerizable functional group-containing organosilicon compound of the present invention may include either a single such structure, or two or more such structures, and if two or more such other structures exist, these structures may be either the same or different. Specific examples of these other structures include alkyl groups of 1 to 10 carbon atoms such as a methyl group, ethyl group, propyl group, isopropyl group, butyl group, isobutyl group, tert-butyl group, pentyl group, hexyl group, heptyl group, octyl group, nonyl group or decyl group.

<Examples of the Radiation-Polymerizable Functional Group-Containing Organosilicon Compound>

There are no particular restrictions on the radiation-polymerizable functional group-containing organosilicon compound of the present invention, provided it includes all of the structures (A) to (C). However, in terms of enhancing the heat resistance stability of the organosilicon compound of the present invention, the carbon atom within the structure (A) to which the structure (B) is directly bonded is preferably different from the carbon atom within the structure (A) to which the structure (C) is bonded, either directly or via the linking group. Particularly preferred compounds include those in which the structure (B) is bonded to either the carbon atom at position 2 or position 3, or the carbon atom at position 5 or position 6 of the structure (A), and the structure (C) is bonded, either directly or via the linking group, to the other position to which the structure (B) is not bonded.

Examples of preferred forms of the radiation-polymerizable functional group-containing organosilicon compound of the present invention include organosilicon compounds represented by a general formula (1) shown below:

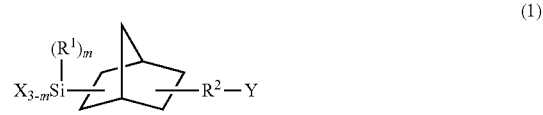

(wherein, each X represents, independently, a halogen atom, an alkoxy group of 1 to 10 carbon atoms, a phenyloxy group, or an acetoxy group, Y represents an acryloyloxy group or a methacryloyloxy group, $R^1$ represents an alkyl group of 1 to 10 carbon atoms, $R^2$ represents an alkylene group of 1 to 10 carbon atoms that either contains, or does not contain, an oxygen atom, a sulfur atom, a nitrogen atom, or a combination thereof, and m represents an integer from 0 to 2).

Of the compounds represented by the general formula (1), the silyl group portion represented by the general formula (1′) shown below corresponds with the hydrolyzable silyl group of the structure (B):

(wherein, X, $R^1$ and m are as defined above),
whereas the portion represented by the general formula (1″) shown below corresponds with the combination of the radiation-polymerizable functional group of the structure (C) and the linking group:

(wherein, Y and $R^2$ are as defined above).

In those cases where X is a halogen atom, examples include a fluorine atom, chlorine atom, bromine atom or iodine atom.

In those cases where X is an alkoxy group, the group contains from 1 to 10 carbon atoms, typically from 1 to 8 carbon atoms, preferably from 1 to 6 carbon atoms, and more preferably from 1 to 4 carbon atoms. Specific examples of the alkoxy group include a methoxy group, ethoxy group, propoxy group, isopropoxy group, butoxy group, isobutoxy group, tert-butoxy group, pentyloxy group, hexyloxy group, heptyloxy group, octyloxy group, nonyloxy group or decyloxy group.

The group X is preferably a methoxy group or ethoxy group.

The group $R^1$ contains from 1 to 10 carbon atoms, typically from 1 to 8 carbon atoms, preferably from 1 to 6 carbon atoms, and more preferably from 1 to 4 carbon atoms. Examples of $R^1$ include a methyl group, ethyl group, propyl group, isopropyl group, butyl group, isobutyl group, tert-butyl group, pentyl group, hexyl group, heptyl group, octyl group, nonyl group or decyl group. Of these, a methyl group or ethyl group is preferred.

The group $R^2$ contains from 1 to 10 carbon atoms, typically from 1 to 8 carbon atoms, preferably from 1 to 6 carbon atoms, and more preferably from 1 to 3 carbon atoms.

In those cases where $R^2$ does not include an oxygen atom, sulfur atom, nitrogen atom or a combination thereof, specific examples of $R^2$ include alkylene groups such as a methylene group, ethylene group, methylmethylene group, propylene group (trimethylene group or methylethylene group), butylene group (such as a tetramethylene group, 1,2-butylene group, 1,3-butylene group or 2,3-butylene group), pentene group (such as a pentamethylene group), hexene group (such as a hexamethylene group), heptene group (such as a heptamethylene group), octene group (such as an octamethylene group), nonene group (such as a nonamethylene group) or decene group (such as a decamethylene group). Of these, linear alkylene groups such as methylene group, ethylene group, trimethylene group, tetramethylene group, pentamethylene group, hexamethylene group, heptamethylene group, octamethylene group, nonamethylene group or decamethylene group are preferred, and a methylene group is particularly desirable.

In those cases where $R^2$ contains an oxygen atom, sulfur atom, nitrogen atom or a combination thereof, specific examples of $R^2$ include divalent groups represented by the formulas shown below.

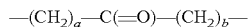
—$(CH_2)_a$—C(=O)—$(CH_2)_b$—

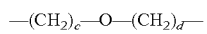
—$(CH_2)_c$—O—$(CH_2)_d$—

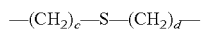
—$(CH_2)_e$—S—$(CH_2)_d$—

—$(CH_2)_e$—N($(CH_2)_f$H)—$(CH_2)_g$—

(wherein, a and b each represents an integer from 1 to 8, provided that a+b is an integer from 2 to 9, c and d each represents an integer from 1 to 9, provided that c+d is an integer from 2 to 10, e and g each represents an integer from 1 to 9, and f represents an integer from 0 to 8, provided that e+f+g is an integer from 2 to 10.)

m is an integer from 0 to 2, and is typically 0.

More preferred examples of the radiation-polymerizable functional group-containing organosilicon compound of the present invention include organosilicon compounds represented by a general formula (2) shown below:

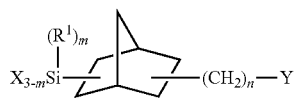

(2)

(wherein, X, Y, $R^1$ and m are as defined above, and n represents an integer from 1 to 10).

n represents an integer from 1 to 10, preferably an integer from 1 to 8, more preferably an integer from 1 to 6, and even more preferably an integer from 1 to 3.

Particularly preferred examples of the radiation-polymerizable functional group-containing organosilicon compound of the present invention include organosilicon compounds represented by a general formula (3) shown below:

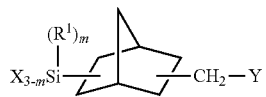

(3)

(wherein, X, Y, $R^1$ and m are as defined above).

Specific examples of the radiation-polymerizable functional group-containing organosilicon compound of the present invention include the compounds shown below.

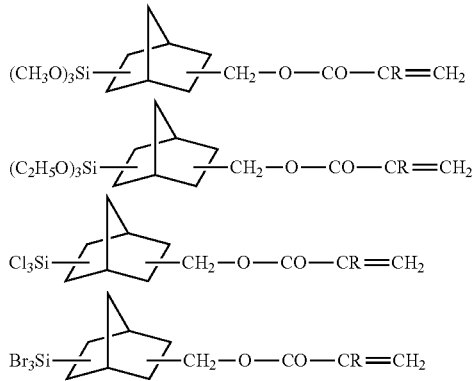

(wherein, R represents a hydrogen atom or a methyl group.)

The radiation-polymerizable functional group-containing organosilicon compound of the present invention may be either a pure compound or a mixture of isomers. Examples of possible isomeric mixtures include mixtures containing an endo isomer and an exo isomer, and mixtures of regioisomers. Examples of regioisomeric mixtures include a mixture of isomers in which, in the general formula (1), the position on the norbornane skeleton structure to which the hydrolyzable silyl group of the structure (B) is directly bonded is a mixture of position 2 and position 3, and a mixture of isomers in which, in the general formula (1), the position on the norbornane skeleton structure to which the radiation-polymerizable functional group of the structure (C) is directly or indirectly bonded is a mixture of position 5 and position 6.

[Haloalkyl Group-Containing Organosilicon Compound]

A haloalkyl group-containing organosilicon compound of the present invention comprises:

(D) a norbornane skeleton structure, (E) a hydrolyzable silyl group bonded directly to the norbornane skeleton structure, and (F) a haloalkyl group, which is bonded directly to the norbornane skeleton structure, and either contains or does not contain a hetero atom.

<(D) Norbornane Skeleton Structure>

The definition, configuration, and specific examples of the norbornane skeleton structure of the structure (D) are as described above in the section entitled "<(A) Norbornane Skeleton Structure>".

<(E) Hydrolyzable Silyl Group>

The structure (E) is a hydrolyzable silyl group that is bonded directly to the norbornane skeleton structure of the structure (D). The haloalkyl group-containing organosilicon compound of the present invention may include either a single hydrolyzable silyl group of the structure (E), or two or more such hydrolyzable silyl groups, and if two or more hydrolyzable silyl groups exist, these groups may be either the same or different. Specific examples of the hydrolyzable silyl group of the structure (E) are as described above in the section entitled "<(B) Hydrolyzable Silyl Group>".

<(F) Haloalkyl Group>

The structure (F) is a haloalkyl group that is bonded directly to the norbornane skeleton structure of the structure (D), and either contains or does not contain a hetero atom. The haloalkyl group of the structure (F) reacts or copolymerizes with an organic resin to form a bond. The haloalkyl group-containing organosilicon compound of the present invention may include either a single haloalkyl group of the structure (F), or two or more such haloalkyl groups, and if two or more haloalkyl groups exist, the groups may be either the same or different.

Examples of the hetero atom include an oxygen atom, sulfur atom or nitrogen atom. The haloalkyl group of the structure (F) may include either a single hetero atom or two or more hetero atoms, and in the case of two or more hetero atoms, these atoms may be either the same or different. The hetero atom exists between two of the carbon atoms that constitute the haloalkyl group of the structure (F), for example, in the form of a carbonyl group (—C(=O)—), oxy group (—O—), thio group (—S—) or imino group (—NH—). Alternatively, the hetero atom may exist between three carbon atoms in the form of a nitro group (—N<) or the like.

Examples of the haloalkyl group of the structure (F) include haloalkyl groups represented by a general formula (4") shown below.

<Other Structures>

The haloalkyl group-containing organosilicon compound of the present invention may also include other structures besides the structures (D) to (F), provided the inclusion of these other structures does not impair the object of the present invention. If such other structures are included, then the haloalkyl group-containing organosilicon compound of the present invention may include either a single such structure, or two or more such structures, and if two or more such other structures exist, these structures may be either the same or different. Specific examples of these other structures are as described above in the section entitled "<Other Structures>" within the description of the "[Radiation-polymerizable Functional Group-containing Organosilicon Compound]".

<Examples of the Haloalkyl Group-Containing Organosilicon Compound>

There are no particular restrictions on the haloalkyl group-containing organosilicon compound of the present invention, provided it includes all of the structures (D) to (F). However, in terms of enhancing the heat resistance stability of the organosilicon compound of the present invention, the hydrolyzable silyl group of the structure (E) and the haloalkyl group of the structure (F) are preferably bonded directly to mutually different carbon atoms on the norbornane skeleton structure of the structure (D). Compounds in which one of the structures (E) and (F) is bonded directly to the carbon atom at position 2 or position 3, and the other structure is bonded directly to the carbon atom at position 5 or position 6 are particularly desirable.

Examples of preferred forms of the haloalkyl group-containing organosilicon compound of the present invention include organosilicon compounds represented by a general formula (4) shown below:

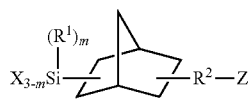
(4)

(wherein, X, $R^1$, $R^2$ and m are as defined above, and Z represents a halogen atom).

Of the compounds represented by the general formula (4), the silyl group portion represented by the general formula (4') shown below corresponds with the hydrolyzable silyl group of the structure (E):

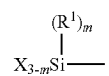
(4')

(wherein, X, $R^1$ and m are as defined above), whereas the portion represented by the general formula (4") shown below corresponds with the haloalkyl group of the structure (F):

$$—R^2—Z \qquad (4'')$$

(wherein, Z and $R^2$ are as defined above).

The group X is preferably a chlorine atom, a methoxy group or an ethoxy group.

Examples of the group Z include a fluorine atom, chlorine atom, bromine atom or iodine atom, and of these, a chlorine atom or bromine atom is preferred.

More preferred examples of the haloalkyl group-containing organosilicon compound of the present invention include organosilicon compounds represented by a general formula (5) shown below:

(5)

(wherein, X, Z, $R^1$, m and n are as defined above).

Particularly preferred examples of the haloalkyl group-containing organosilicon compound of the present invention include organosilicon compounds represented by a general formula (6) shown below:

(6)

(wherein, X, $R^1$ and m are as defined above, and Z' represents a bromine atom or a chlorine atom).

Specific examples of the haloalkyl group-containing organosilicon compound of the present invention include the compounds shown below.

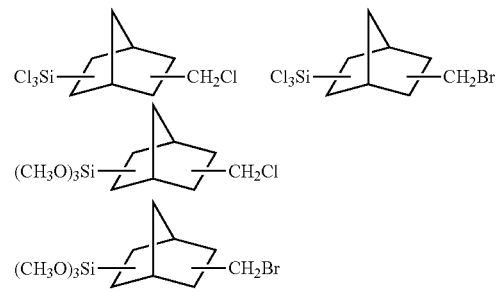

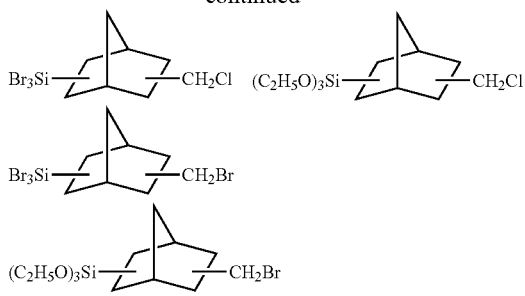

The haloalkyl group-containing organosilicon compound of the present invention may be either a pure compound or a mixture of isomers. Examples of possible isomeric mixtures include mixtures containing an endo isomer and an exo isomer, and mixtures of regioisomers. Examples of regioisomeric mixtures include a mixture of isomers in which, in the general formula (4), the position on the norbornane skeleton structure to which the hydrolyzable silyl group of the structure (E) is directly bonded is a mixture of position 2 and position 3, and a mixture of isomers in which, in the general formula (4), the position on the norbornane skeleton structure to which the haloalkyl group of the structure (F) is directly bonded is a mixture of position 5 and position 6.

[Method of Producing Radiation-Polymerizable Functional Group-Containing Organosilicon Compound]

The radiation-polymerizable functional group-containing organosilicon compound of the present invention comprising the structures (A) to (C) can be produced, for example, by conducting a desalting reaction between a haloalkyl group-containing organosilicon compound, comprising (D) a norbornane skeleton structure, (E) a hydrolyzable silyl group bonded directly to the norbornane skeleton structure, and (F) a haloalkyl group, which is bonded directly to the norbornane skeleton structure, and either contains or does not contain a hetero atom, and at least one salt having a radiation-polymerizable functional group, selected from the group consisting of alkali metal salts of organic acids having a radiation-polymerizable functional group and alkaline earth metal salts of organic acids having a radiation-polymerizable functional group, at a temperature within a range from 50 to 150° C.

<Haloalkyl Group-Containing Organosilicon Compound>

The haloalkyl group-containing organosilicon compound is as described above. There are no particular restrictions on the haloalkyl group of the structure (F), provided it is capable of producing a radiation-polymerizable functional group of the structure (C) via the desalting reaction with the salt having a radiation-polymerizable functional group. In those cases where the targeted organosilicon compound is an organosilicon compound represented by the above general formula (1), a compound represented by the above general formula (4) can be used as the haloalkyl group-containing organosilicon compound. In those cases where the targeted organosilicon compound is an organosilicon compound represented by the above general formula (2), a compound represented by the above general formula (5) can be used as the haloalkyl group-containing organosilicon compound. In those cases where the targeted organosilicon compound is an organosilicon compound represented by the above general formula (3), a compound represented by the above general formula (6) can be used as the haloalkyl group-containing organosilicon compound.

<Salt Having a Radiation-Polymerizable Functional Group>

The salt having a radiation-polymerizable functional group is at least one salt selected from the group consisting of alkali metal salts of organic acids having a radiation-polymerizable functional group and alkaline earth metal salts of organic acids having a radiation-polymerizable functional group. Examples of the organic acids having a radiation-polymerizable functional group include acrylic acid and methacrylic acid. Examples of the alkali metals include lithium, sodium and potassium, and sodium and potassium are preferred. Examples of the alkaline earth metals include calcium, strontium and barium, and calcium is preferred.

Examples of the salt having a radiation-polymerizable functional group include acrylic acid salts and methacrylic acid salts represented by a general formula (10) shown below:

$$Y\text{-}M \tag{10}$$

(wherein, Y is as defined above, and M represents an alkali metal atom or an alkaline earth metal atom), namely, alkali metal salts and alkaline earth metal salts of acrylic acid and methacrylic acid. Specific examples of the acrylic acid salts and methacrylic acid salts represented by the general formula (10) include potassium acrylate, potassium methacrylate, sodium acrylate, sodium methacrylate, lithium acrylate and lithium methacrylate. Of these, from the viewpoint of reactivity, potassium acrylate, potassium methacrylate, sodium acrylate and sodium methacrylate are preferred, and potassium acrylate and potassium methacrylate are particularly desirable.

<Conditions for Desalting Reaction>

There are no particular restrictions on the blend ratio between the haloalkyl group-containing organosilicon compound and the salt having a radiation-polymerizable functional group, although in terms of reactivity and productivity, the reaction is preferably conducted using a quantity of the salt having a radiation-polymerizable functional group that is within a range from 0.8 to 2 mols, and preferably from 0.8 to 1.2 mols, per 1 mol of the haloalkyl group-containing organosilicon compound.

In the synthesis of the radiation-polymerizable functional group-containing organosilicon compound of the present invention, the desalting reaction is preferably conducted under heating and within an organic solvent in order to accelerate the reaction rate.

The organic solvent is preferably an organic solvent that contains no active hydrogen, and of such solvents, polar organic solvents are particularly desirable. Specific examples of the organic solvent include saturated hydrocarbon-based solvents such as pentane, hexane, cyclohexane, heptane and decane; ether-based solvents such as diethyl ether, tetrahydrofuran and dioxane; ester-based solvents such as ethyl acetate and butyl acetate; polyether-based solvents such as triethylene glycol dimethyl ether; aromatic solvents such as benzene, toluene and xylene; ketone-based solvents such as acetone, methyl ethyl ketone, and methyl isobutyl ketone; and amide-based solvents such as formamide and dimethylformamide. Of these organic solvents, dimethylformamide and toluene are particularly preferred in terms of the degree of polarity and the boiling point. A single organic solvent may be used alone, or a combination of two or more different solvents may be used.

The reaction temperature must be set within the range from 50 to 150° C., and is preferably from 80 to 130° C. If the temperature is lower than 50° C., then the desalting reaction tends to proceed poorly, whereas if the temperature exceeds 150° C., there is a possibility that the produced radiation-polymerizable functional group-containing organosilicon compound may polymerize.

When conducting the reaction, a polymerization inhibitor is preferably used to stabilize the produced radiation-polymerizable functional group-containing organosilicon compound. Typical commercially available products may be used as this polymerization inhibitor, and hindered phenol-based compounds are particularly desirable. The quantity added of the polymerization inhibitor need only be a typical quantity for a polymerization inhibitor. For example, a quantity of 0.001 to 1.0% by mass relative to the radiation-polymerizable functional group-containing organosilicon compound is preferred.

<Purification Method>

The alkali metal halide or alkaline earth metal halide generated as a result of the desalting reaction can be separated from the target radiation-polymerizable functional group-containing organosilicon compound using techniques such as filtration that are well known to those skilled in the art. The radiation-polymerizable functional group-containing organosilicon compound can be further purified using methods such as distillation under reduced pressure or liquid column chromatography that are also well known to those skilled in the art.

[Method of Producing Haloalkyl Group-Containing Organosilicon Compound]

<Production Method 1>

The haloalkyl group-containing organosilicon compound comprising the structures (D) to (F) can be produced, for example, by subjecting a hydrolyzable silane having a hydrogen atom bonded directly to the silicon atom (hereafter also referred to as a "SiH group"), and a norbornene derivative having a norbornene skeleton structure and a haloalkyl group that is bonded directly to the norbornene skeleton structure and either contains or does not contain a hetero atom, to a hydrosilylation reaction in the presence of a catalyst.

Hydrolyzable Silane Having a SiH Group

There are no particular restrictions on the hydrolyzable silane having a SiH group, provided it is capable of generating a hydrolyzable silyl group of the structure (E) via a hydrosilylation reaction with the above norbornene derivative.

In those cases where the haloalkyl group-containing organosilicon compound is an organosilicon compound represented by one of the general formulas (4) to (6) shown above, examples of the hydrolyzable silane having a SiH group include compounds represented by a general formula shown below:

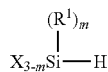

(wherein, X, $R^1$ and m are as defined above).

Norbornene Derivative

The norbornene derivative has a norbornene skeleton structure and a haloalkyl group that is bonded directly to the norbornene skeleton structure and either contains or does not contain a hetero atom. In this description, a "norbornene skeleton structure" refers to an atom grouping that remains when at least one hydrogen atom are removed from a structure in which a carbon-carbon double bond is formed between at least one pair of adjacent carbon atoms within norbornane. Provided the valency of the norbornene skeleton structure is monovalent or higher, there are no particular restrictions on the number of carbon-carbon double bonds or on the position of each double bond.

The norbornene derivative may include either a single haloalkyl group or two or more haloalkyl groups within the norbornene skeleton structure, and if two or more haloalkyl groups exist, these groups may be either the same or different.

Examples of the hetero atom and its configuration within the haloalkyl group are as described above in the section entitled "<(F) Haloalkyl Group>".

In those cases where the haloalkyl group-containing organosilicon compound is an organosilicon compound represented by the above general formula (4), examples of the norbornene derivative include compounds represented by a general formula (7) shown below:

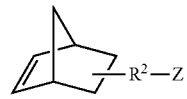

(7)

(wherein, $R^2$ and Z are as defined above).

In those cases where the haloalkyl group-containing organosilicon compound is an organosilicon compound represented by the above general formula (5), compounds represented by the general formula (7) in which $R^2$ is a —$(CH_2)_n$— group can be used as the norbornene derivative. Furthermore, in those cases where the haloalkyl group-containing organosilicon compound is an organosilicon compound represented by the above general formula (6), compounds represented by the general formula (7) in which $R^2$ is a —$CH_2$— group and Z is Z' can be used as the norbornene derivative.

The norbornene derivative may use a compound commercially available from any of the various chemical manufacturers, or may use a reaction product obtained using a conventional method in which an olefin compound capable of generating the haloalkyl group and cyclopentadiene are subjected to a Diels Alder reaction. For example, a norbornene derivative represented by the above general formula (7) can be prepared in accordance with this conventional method by subjecting an olefin compound represented by a general formula shown below:

and cyclopentadiene to a Diels Alder reaction.

<Production Method 2>

Among the haloalkyl group-containing organosilicon compound comprising the structures (D) to (F), an organosilicon compound comprising:

(D) a norbornane skeleton structure, (E') an organooxysilyl group bonded directly to the norbornane skeleton structure, and (F) a haloalkyl group, which is bonded directly to the norbornane skeleton structure, and either contains or does not contain a hetero atom can be produced by:

using a halosilane having a SiH group as the hydrolyzable silane having a SiH group from the production method 1, conducting the hydrosilylation reaction of the production method 1 to obtain an organosilicon compound comprising:

(D) a norbornane skeleton structure, (E") a halosilyl group bonded directly to the norbornane skeleton structure, and (F) a haloalkyl group, which is bonded directly to the norbornane skeleton structure, and either contains or does not contain a hetero atom, and then following the hydrosilylation reaction, reacting the organosilicon compound comprising (D), (E") and (F) with a hydroxyl group-containing organic compound.

Organosilicon Compound Comprising Structures (D), (E') and (F)

With the exception of restricting the structure (E) to the structure (E'), the organosilicon compound comprising the structures (D), (E') and (F) is the same as the organosilicon compound comprising the structures (D) to (F).

The structure (E') is an organooxysilyl group that is bonded directly to the norbornane skeleton structure of the structure (D). The organosilicon compound comprising the structures (D), (E') and (F) may include either a single organooxysilyl group of the structure (E'), or two or more such organooxysilyl groups, and if two or more organooxysilyl groups exist, the groups may be either the same or different.

Examples of the organosilicon compound comprising the structures (D), (E') and (F) include compounds represented by a general formula (8) shown below:

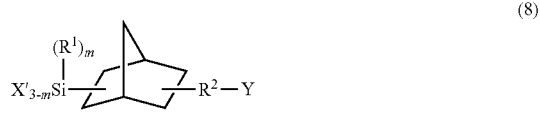

(8)

(wherein, each X' represents, independently, an alkoxy group of 1 to 10 carbon atoms, a phenyloxy group or an acetoxy group, and Z, $R^1$, $R^2$ and m are as defined above).

In those cases where X' represents an alkoxy group, the typical and preferred ranges for the number of carbon atoms within the group, and specific examples of the alkoxy group are as described above for the group X.

Halosilane Having a SiH Group

There are no particular restrictions on the halosilane having a SiH group, provided it is capable of generating a halosilyl group of the structure (E") via a hydrosilylation reaction with the above norbornene derivative.

In those cases where the haloalkyl group-containing organosilicon compound is an organosilicon compound represented by the above general formula (8), compounds represented by a general formula shown below can be used as the halosilane.

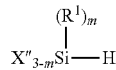

(wherein, X" represents a halogen atom, and $R^1$ and m are as defined above.)

Organosilicon Compound Comprising Structures (D), (E") and (F)

With the exception of restricting the structure (E) to the structure (E"), the organosilicon compound comprising the structures (D), (E") and (F) is the same as the organosilicon compound comprising the structures (D) to (F).

The structure (E") is an halosilyl group that is bonded directly to the norbornane skeleton structure of the structure (D). The organosilicon compound comprising the structures (D), (E") and (F) may include either a single halosilyl group of the structure (E"), or two or more such halosilyl groups, and if two or more halosilyl groups exist, the groups may be either the same or different.

In those cases where the haloalkyl group-containing organosilicon compound is an organosilicon compound represented by the above general formula (8), examples of the organosilicon compound comprising the structures (D), (E") and (F) include compounds represented by a general formula (9) shown below:

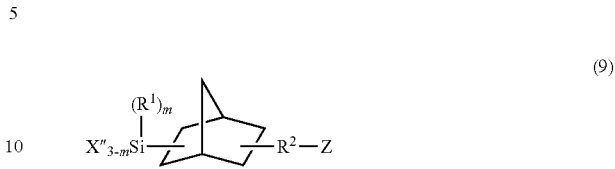

(9)

(wherein, X", Z, $R^1$, $R^2$ and m are as defined above).

Hydroxyl Group-Containing Organic Compound

There are no particular restrictions on the hydroxyl group-containing organic compound, provided it reacts with the halosilyl group of the structure (E") to generate the organooxysilyl group of the structure (E'). Examples of the hydroxyl group-containing compound include alcohols, phenols and carboxylic acids.

In those cases where the haloalkyl group-containing organosilicon compound is an organosilicon compound represented by the above general formula (8), examples of the hydroxyl group-containing organic compound include compounds represented by a general formula shown below:

X'—H (wherein, X' is as defined above).

Of these compounds, methanol and ethanol are preferred.

<Reaction Conditions>

Hydrosilylation Reaction

In a hydrosilylation reaction, the use of a catalyst composed of a heavy metal complex or the like is conventional, and in the hydrosilylation reaction within the production method of the present invention, a heavy metal complex such as a palladium complex, platinum complex or rhodium complex is typically used as a catalyst. Of these complexes, in terms of the reactivity and the quantity of catalyst used, a palladium complex or a platinum complex is preferred, and from the viewpoint of reactivity, a palladium complex is particularly desirable.

Although there are no particular restrictions on the quantity of catalyst used, from the viewpoints of reactivity and productivity, the quantity is typically within a range from 0.000001 to 0.01 mols, and preferably from 0.00001 to 0.001 mols, per 1 mol of the norbornene derivative. Provided the quantity of the catalyst is within this range, a satisfactory reaction acceleration effect that corresponds with the quantity of the catalyst is readily obtained.

There are no particular restrictions on the blend ratio between the hydrolyzable silane having a SiH group and the norbornene derivative, but from the viewpoints of reactivity and productivity, a quantity of the hydrolyzable silane having a SiH group within a range from 0.5 to 2 mols, and particularly from 0.8 to 1.2 mols, is preferably reacted with each 1 mol of the norbornene derivative.

During the hydrosilylation reaction, in addition to the catalyst described above, an auxiliary agent that controls the catalyzed reaction may also be added. Conventional materials may be used as this auxiliary agent, and specific examples include organophosphorus compounds, phosphite ester compounds, and organonitrogen compounds.

The hydrosilylation reaction is usually conducted as a solventless reaction, although solvent dilution may be used to facilitate reaction control. In such cases, there are no particular restrictions on the solvent, provided it exhibits no reactivity with the raw materials used and has no other adverse effects such as catalyst poisoning. Specific examples of the solvent include hydrocarbon-based solvents such as pentane, hexane, cyclohexane, benzene, toluene and xylene; ether-based solvents such as diethyl ether, tetrahydrofuran and dioxane; ester-based solvents such as ethyl acetate and butyl acetate; aprotic polar solvents such as acetonitrile and dimethylformamide; and chlorinated hydrocarbon solvents such as dichloromethane and chloroform. A single solvent may be used alone, or a combination of a plurality of different solvents may be used.

Although there are no particular restrictions on the reaction temperature, provided it is a temperature at which the hydrosilylation proceeds, the temperature is typically within a range from 0 to 200° C., and preferably from 10 to 150° C.

Organooxylation Reaction

In this description, the term "organooxylation reaction" describes the reaction following the hydrosilylation reaction of the above production method 2, wherein the organosilicon compound comprising the structures (D), (E") and (F) is reacted with the hydroxyl group-containing organic compound, thereby converting the halosilyl group of the structure (E") to the organooxysilyl group of the structure (E'). Specifically, in those cases where the hydroxyl group-containing organic compound is an alcohol, the organooxylation reaction refers to an alkoxylation reaction. More specifically, if the hydroxyl group-containing organic compound is methanol, then the organooxylation reaction refers to a methoxylation reaction.

The organooxylation reaction proceeds spontaneously even without a catalyst, although from the viewpoints of reactivity and productivity, the reaction is preferably conducted in the presence of urea, a tertiary amine or a metal alkoxide or the like, which acts as a scavenger for the generated hydrogen halide.

Although there are no particular restrictions on the quantity of this scavenger, from the viewpoints of reactivity and productivity, the quantity is typically within a range from 0.5 to 1.5 mols, and preferably from 0.8 to 1.2 mols, per 1 mol of halogen atoms within the structure (E") of the organosilicon compound comprising the structures (D), (E") and (F). Provided the quantity of the scavenger is within this range, a satisfactory reaction acceleration effect that corresponds with the quantity of the scavenger is readily obtained.

There are no particular restrictions on the blend ratio between the organosilicon compound comprising the structures (D), (E") and (F) and the hydroxyl group-containing organic compound, but from the viewpoints of reactivity and productivity, the blend quantity is preferably adjusted so that the quantity of hydroxyl groups within the hydroxyl group-containing organic compound is within a range from 1 to 3 mols, and particularly from 1 to 2 mols, per 1 mol of halogen atoms within the structure (E") of the organosilicon compound.

Although there are no particular restrictions on the reaction temperature, provided it is a temperature at which the organooxylation reaction proceeds satisfactorily, the temperature is typically within a range from 50 to 80° C., and preferably from 60 to 70° C.

EXAMPLES

A description of specifics of the present invention is provided below based on a series of synthesis examples and examples, although the present invention is in no way limited by the examples presented below. In the examples, GC is an abbreviation for Gas Chromatography, NMR is an abbreviation for Nuclear Magnetic Resonance spectroscopy, IR is an abbreviation for Infra Red spectroscopy, and bp is an abbreviation for boiling point.

Synthesis Example 1

A 2-liter autoclave fitted with a stirrer, a thermometer and a heater was charged with 488.5 g (3.7 mols) of dicyclopentadiene, 1074.7 g (8.9 mols) of allyl bromide and 3.1 g of hydroquinone, and the resulting mixture was stirred under heating at 150° C., under sealed conditions and at normal pressure. After 20 hours, GC was used to confirm that the raw material peaks had disappeared and a new peak attributable to the reaction product had appeared, and the reaction was halted at this point. The reaction product was distilled under reduced pressure, yielding a pale yellow transparent liquid (bp: 54 to 56° C., 3 mmHg) at a yield of 70%. GC confirmed that the purity of the reaction product was 98%. Furthermore, $^1$H NMR and $^{13}$C NMR confirmed that the reaction product was 5-bromomethyl-2-norbornene, and was a mixture of the endo and exo isomers.

$^1$H NMR (300 MHz, CDCl$_3$, δ (ppm)): main isomer (the endo isomer) 0.56 (m, 1H), 1.27 (d, J=8.2 Hz, 1H), 1.45 (m, 1H), 1.91 (m, 1H), 2.48 (m, 1H), 2.84 (s, 1H), 2.96 (s, 1H), 3.00 (dd, J=6.9 Hz, 9.6 Hz, 1H), 3.17 (dd, J=6.9 Hz, 9.6 Hz, 1H), 5.96 (m, 1H), 6.17 (m, 1H).

$^{13}$C NMR (75 MHz, CDCl$_3$, δ (ppm)): main isomer (the endo isomer) 32.6, 38.0, 42.0, 43.0, 45.3, 49.5, 131.4, 138.0.

Synthesis Example 2

With the exceptions of using 679.5 g (8.9 mols) of allyl chloride instead of the 1074.7 g (8.9 mols) of allyl bromide used in the synthesis example 1, and altering the quantity of hydroquinone from 3.1 g to 2.4 g, reaction and subsequent distillation under reduced pressure were conducted in the same manner as the synthesis example 1, yielding a colorless transparent liquid (bp: 80 to 82° C., 50 mmHg) at a yield of 57%. GC confirmed that the purity of the reaction product was 98%. Furthermore, $^1$H NMR and $^{13}$C NMR confirmed that the reaction product was 5-chloromethyl-2-norbornene, and was a mixture of the endo and exo isomers.

$^1$H NMR (300 MHz, CDCl$_3$, δ (ppm)): main isomer (the endo isomer) 0.56 (m, 1H), 1.27 (d, J=8.2 Hz, 1H), 1.45 (m, 1H), 1.91 (m, 1H), 2.48 (m, 1H), 2.84 (s, 1H), 2.96 (s, 1H), 3.00 (dd, J=6.9 Hz, 9.6 Hz, 1H), 3.17 (dd, J=6.9 Hz, 9.6 Hz, 1H), 5.96 (m, 1H), 6.17 (m, 1H).

$^{13}$C NMR (75 MHz, CDCl$_3$, δ (ppm)): main isomer (the endo isomer) 31.2, 41.8, 42.6, 44.5, 48.5, 49.3, 131.6, 137.9.

Example 1

Figure 2:
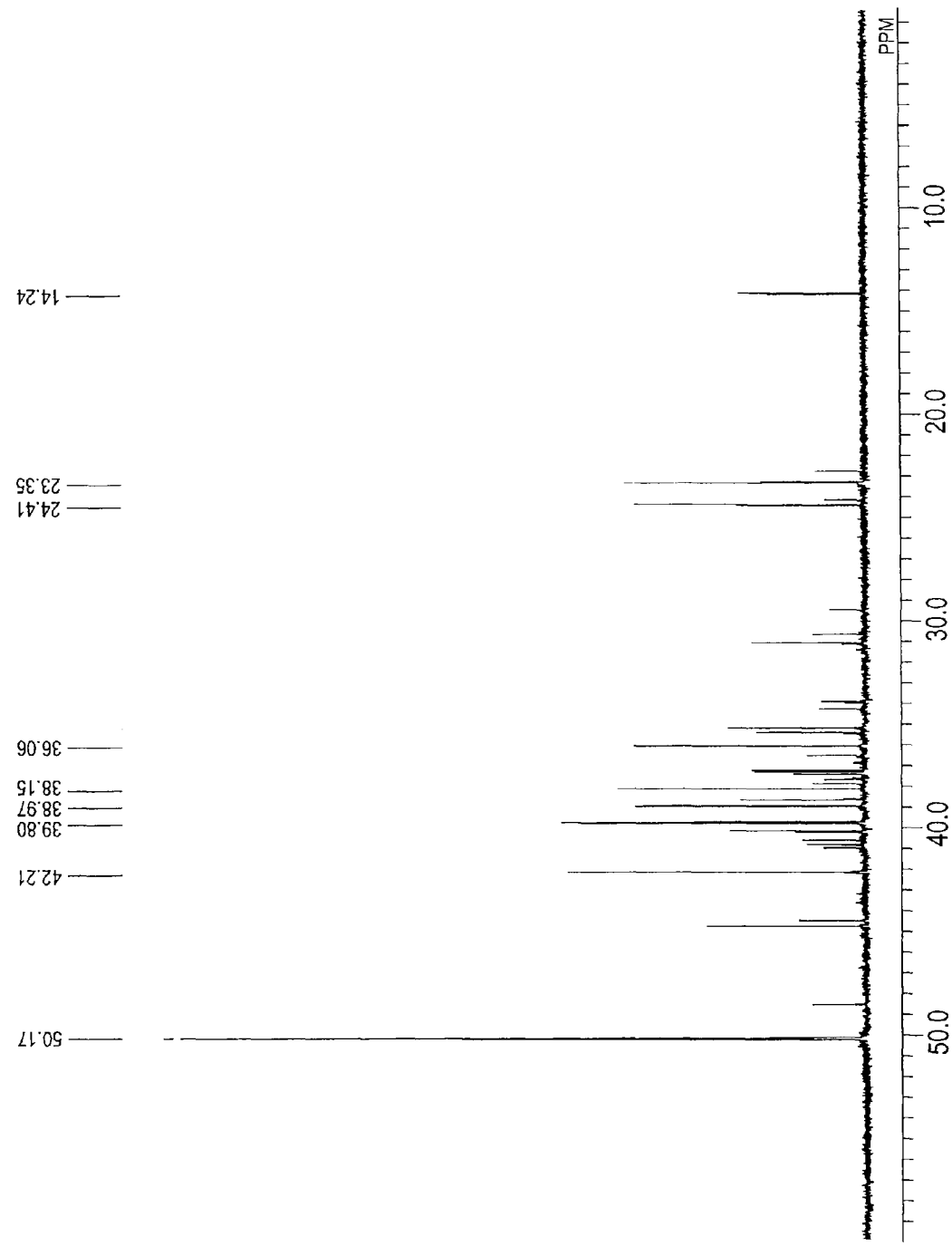
FIG. 2 is a diagram showing the $^{13}$C NMR spectrum of the reaction product of the example 1.
Figure 3:
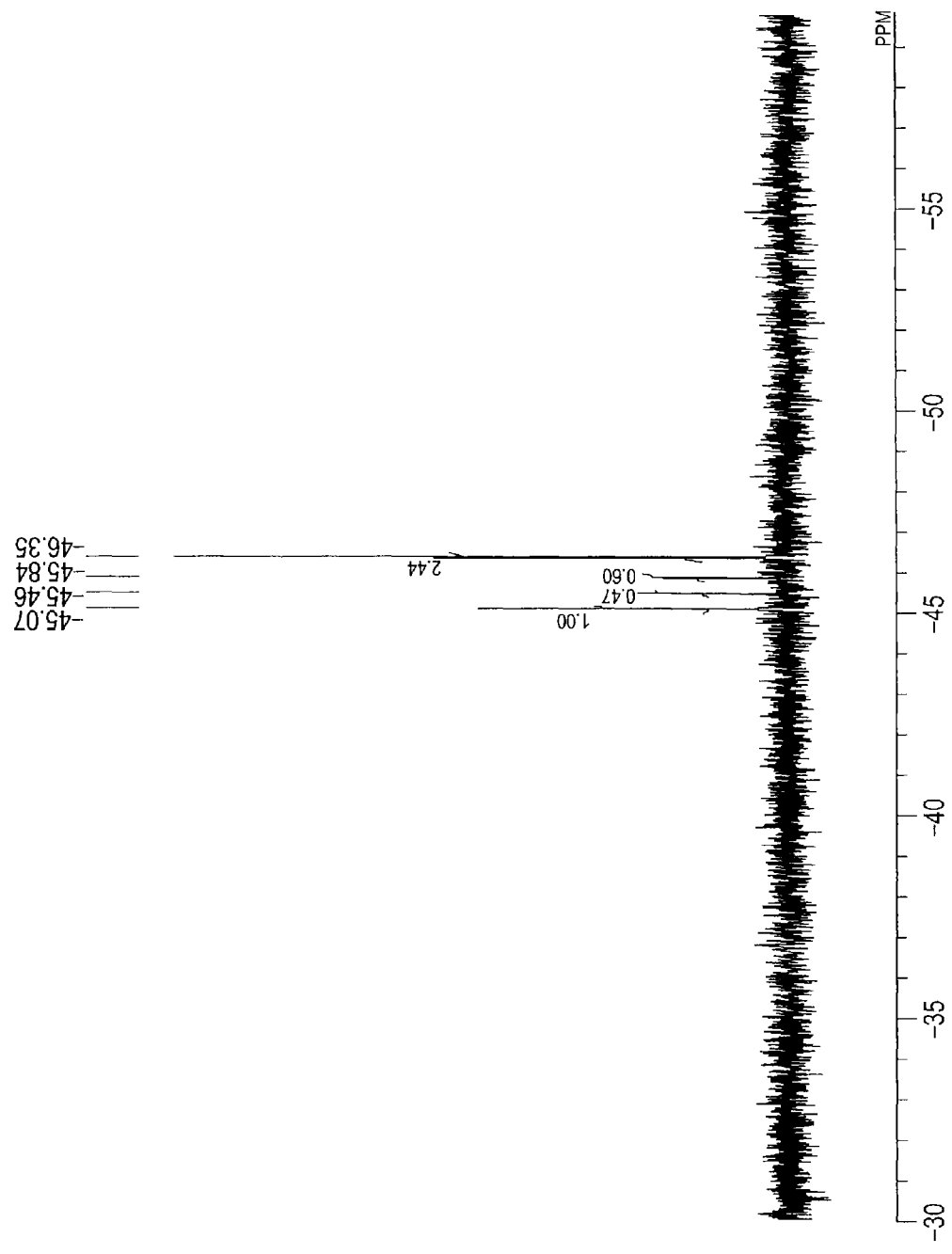
FIG. 3 is a diagram showing the $^{29}$Si NMR spectrum of the reaction product of the example 1.

A 1-liter separable flask fitted with a stirrer, a reflux condenser, a dropping funnel and a thermometer was charged with 150 g (0.802 mols) of 5-bromomethyl-2-norbornene, 45.6 mg of dichloro(1,5-cyclooctadiene) palladium and 89.6 mg of tricyclohexylphosphine, and the mixture was heated to 135° C. Once the internal temperature had stabilized, 130.4 g (0.963 mols) of trichlorosilane was added dropwise over a period of 4 hours. Following completion of the dropwise addition, the reaction mixture was stirred at 135° C. After 2 hours, GC was used to confirm that the raw material peak had disappeared and a new peak attributable to the reaction product had appeared, and the hydrosilylation reaction was halted at this point. The temperature of the reaction mixture was then cooled to 80° C., and 61.6 g (1.92 mols) of methanol was added dropwise to the mixture. Following completion of the dropwise addition, the reaction mixture was stirred for one hour at 75° C. Subsequently, 69.3 g (1.16 mols) of urea was added to the reaction mixture, and a further 46.2 g (1.44 mols) of methanol was added dropwise. The reaction mixture was stirred for a further 2 hours at 75° C., and the stirring and heating were then halted. Upon standing, the reaction mixture separated into a layer containing a methanol solution of urea hydrochloride and a layer containing the reaction product. The layer containing the reaction product was collected, and then analyzed by GC. This analysis confirmed that the raw material peak had disappeared and a new peak attributable to the reaction product had appeared, and the methoxylation reaction was halted at this point. The reaction product was distilled under reduced pressure, yielding a colorless transparent liquid (bp: 110 to 116° C., 3 to 5 mmHg) at a yield of 93%. GC confirmed that the purity of the reaction product was 95%. Furthermore, $^1$H NMR, $^{13}$C NMR and $^{29}$Si NMR confirmed that the reaction product was 5-bromomethyl-norbornyltrimethoxysilane, was a mixture of endo and exo isomers, and was a mixture of an isomer in which the trimethoxysilyl group was bonded directly to position 2 on the norbornane skeleton structure and an isomer in which the trimethoxysilyl group was bonded directly to position 3 on the norbornane skeleton structure. The NMR spectra of this reaction product are shown in FIG. 1 to FIG. 3.

$^1$H NMR (300 MHz, CDCl$_3$, δ (ppm)): isomeric mixture 0.45 to 3.27 (m, 12H), 3.35 (s, 6H, Si—OCH$_3$), 3.37 (s, 3H, Si—OCH$_3$).

$^{13}$C NMR (75 MHz, CDCl$_3$, δ (ppm)): isomeric mixture (main product only listed) 14.2, 23.4, 24.4, 36.1, 38.2, 39.0, 39.8, 42.2, 50.2 (Si—OCH$_3$).

$^{29}$Si NMR (60 MHz, CDCl$_3$, δ (ppm)): isomeric mixture −45.1, −45.5, −45.8, −46.4.

Example 2

With the exceptions of using 40 mg of a platinum complex composed of vinyldimethyldisiloxane coordinated to chloroplatinic acid as the hydrosilylation catalyst instead of the 45.6 mg of dichloro(1,5-cyclooctadiene) palladium used in the example 1, not using the tricyclohexylphosphine, and altering the temperature prior to the dropwise addition of the trichlorosilane from 135° C. to 120° C., a hydrosilylation reaction, methoxylation reaction, and distillation under reduced pressure were conducted in the same manner as the example 1, yielding a colorless transparent liquid (bp: 110 to 116° C., 3 to 5 mmHg) at a yield of 67%. GC confirmed that the purity of the reaction product was 95%. Furthermore, $^1$H NMR, $^{13}$C NMR and $^{29}$Si NMR confirmed that the reaction product was 5-bromomethyl-norbornyltrimethoxysilane, was a mixture of endo and exo isomers, and was a mixture of an isomer in which the trimethoxysilyl group was bonded directly to position 2 on the norbornane skeleton structure and an isomer in which the trimethoxysilyl group was bonded directly to position 3 on the norbornane skeleton structure. The NMR spectra of this reaction product were the same as those shown in FIG. 1 to FIG. 3.

Example 3

Figure 4:
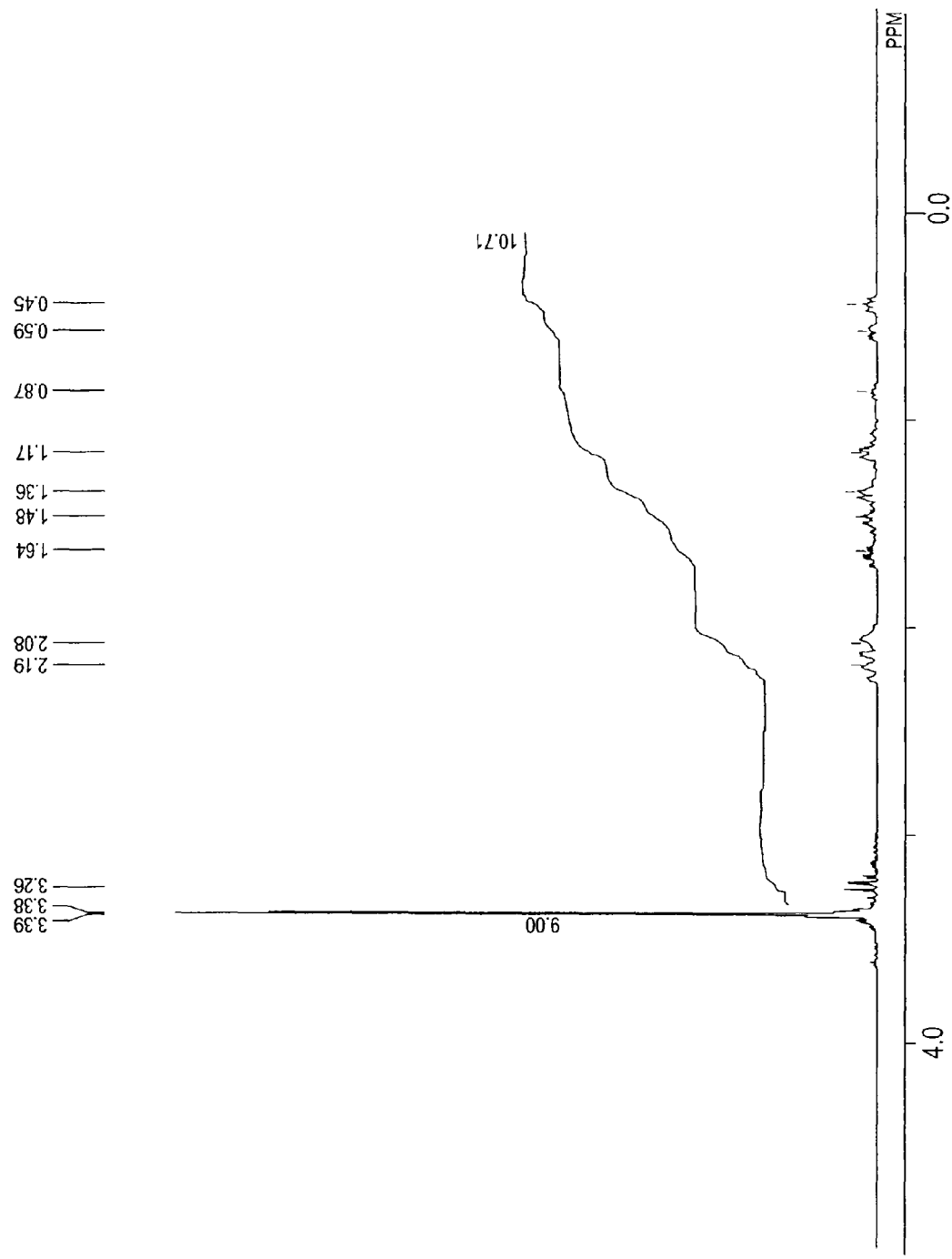
FIG. 4 is a diagram showing the $^1$H NMR spectrum of the reaction product of an example 3.
Figure 5:
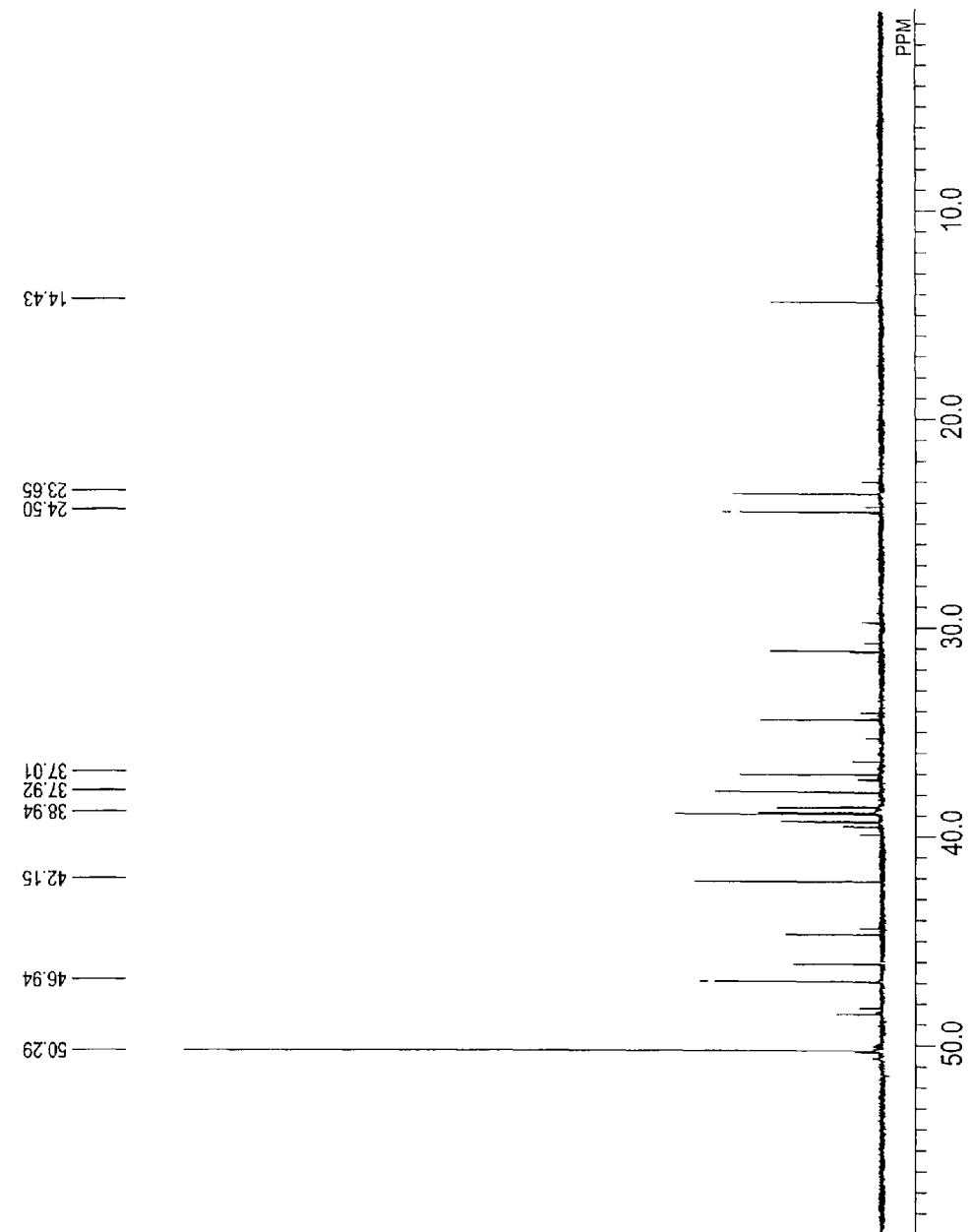
FIG. 5 is a diagram showing the $^{13}$C NMR spectrum of the reaction product of the example 3.
Figure 6:
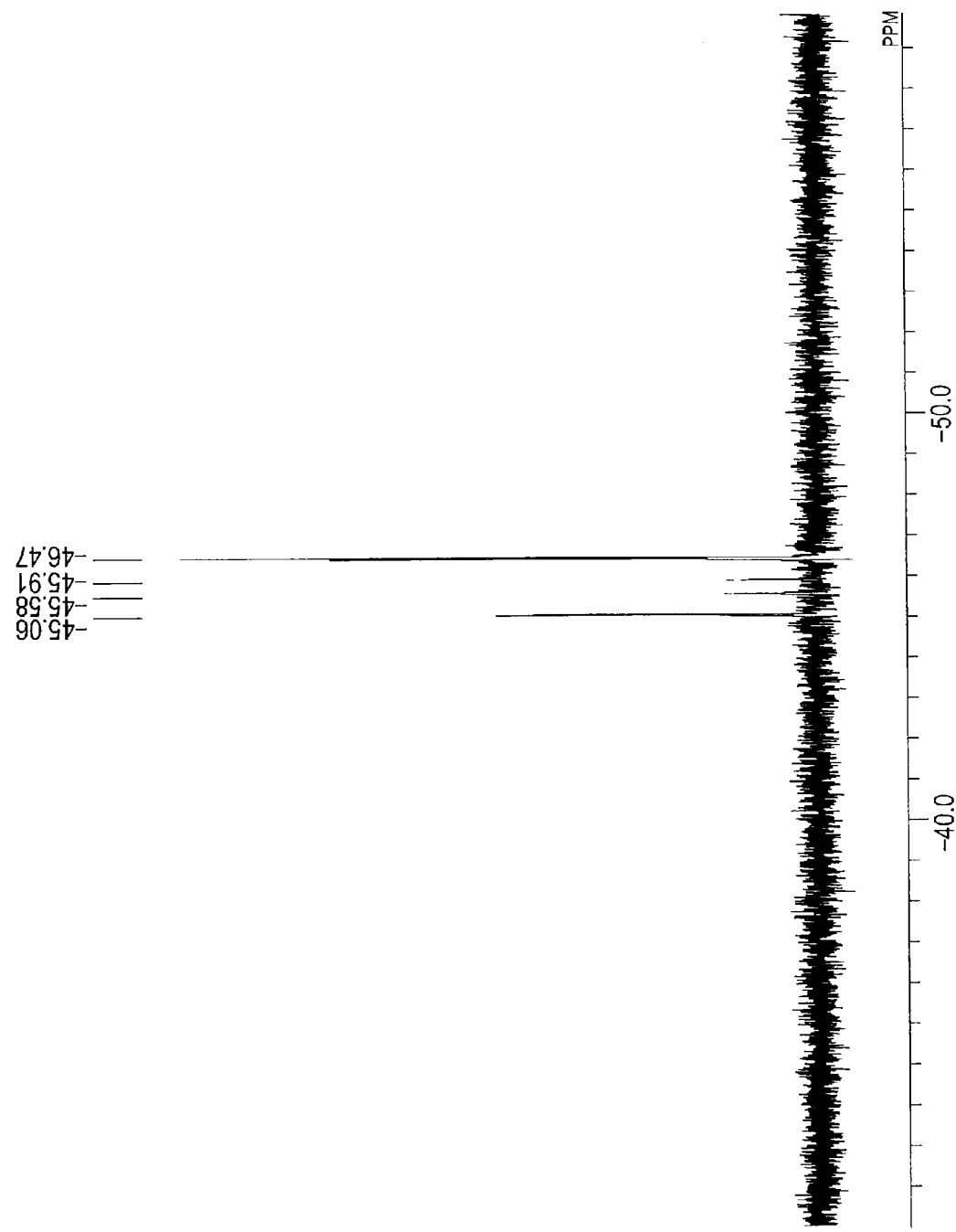
FIG. 6 is a diagram showing the $^{29}$Si NMR spectrum of the reaction product of the example 3.

A 1-liter separable flask fitted with a stirrer, a reflux condenser, a dropping funnel and a thermometer was charged with 290 g (2.03 mols) of 5-chloromethyl-2-norbornene, 0.32 g of dichloro(1,5-cyclooctadiene) palladium and 0.62 g of tricyclohexylphosphine, and the mixture was heated to 135° C. Once the internal temperature had stabilized, 302 g (2.23 mols) of trichlorosilane was added dropwise over a period of 4 hours. Following completion of the dropwise addition, the reaction mixture was stirred at 135° C. After 2 hours, GC was used to confirm that the raw material peak had disappeared and a new peak attributable to the reaction product had appeared, and the hydrosilylation reaction was halted at this point. The temperature of the reaction mixture was then cooled to 80° C., and 142.7 g (4.46 mols) of methanol was added dropwise to the mixture. Following completion of the dropwise addition, the reaction mixture was stirred for one hour at 75° C. Subsequently, 160.6 g (2.67 mols) of urea was added to the reaction mixture, and a further 107.0 g (3.35 mols) of methanol was added dropwise. The reaction mixture was stirred for a further 2 hours at 75° C., and the stirring and heating were then halted. Upon standing, the reaction mixture separated into a layer containing a methanol solution of urea hydrochloride and a layer containing the reaction product. The layer containing the reaction product was collected, and then analyzed by GC. This analysis confirmed that the raw material peak had disappeared and a new peak attributable to the reaction product had appeared, and the methoxylation reaction was halted at this point. The reaction product was distilled under reduced pressure, yielding a colorless transparent liquid (bp: 106 to 108° C., 3 to 5 mmHg) at a yield of 92%. GC confirmed that the purity of the reaction product was 95%. Furthermore, $^1$H NMR, $^{13}$C NMR and $^{29}$Si NMR confirmed that the reaction product was 5-chloromethyl-norbornyltrimethoxysilane, was a mixture of endo and exo isomers, and was a mixture of an isomer in which the trimethoxysilyl group was bonded directly to position 2 on the norbornane skeleton structure and an isomer in which the trimethoxysilyl group was bonded directly to position 3 on the norbornane skeleton structure. The NMR spectra of this reaction product are shown in FIG. 4 to FIG. 6.

$^1$H NMR (300 MHz, CDCl$_3$, δ (ppm)): isomeric mixture 0.45 to 3.26 (m, 12H), 3.38 (s, 6H, Si—OCH$_3$), 3.39 (s, 3H, Si—OCH$_3$).

$^{13}$C NMR (75 MHz, CDCl$_3$, δ (ppm)): isomeric mixture (main product only listed) 14.4, 23.7, 24.5, 37.0, 37.9, 38.9, 42.2, 46.9, 50.3 (Si—OCH$_3$).

$^{29}$Si NMR (60 MHz, CDCl$_3$, δ (ppm)): isomeric mixture −45.1, −45.6, −45.9, −46.5.

Example 4

With the exceptions of using 40 mg of a platinum complex composed of vinyldimethyldisiloxane coordinated to chloroplatinic acid as the hydrosilylation catalyst instead of the 0.32 g of dichloro(1,5-cyclooctadiene) palladium used in the example 3, not using the tricyclohexylphosphine, and altering the temperature prior to the dropwise addition of the trichlorosilane from 135° C. to 120° C., a hydrosilylation reaction, methoxylation reaction, and distillation under reduced pressure were conducted in the same manner as the example 3, yielding a colorless transparent liquid (bp: 106 to 108° C., 3 to 5 mmHg) at a yield of 66%. GC confirmed that the purity of the reaction product was 95%. Furthermore, $^1$H NMR, $^{13}$C NMR and $^{29}$Si NMR confirmed that the reaction product was 5-chloromethyl-norbornyltrimethoxysilane, was a mixture of endo and exo isomers, and was a mixture of an isomer in which the trimethoxysilyl group was bonded directly to position 2 on the norbornane skeleton structure and an isomer in which the trimethoxysilyl group was bonded directly to position 3 on the norbornane skeleton structure. The NMR spectra of this reaction product were the same as those shown in FIG. 4 to FIG. 6.

Example 5

Figure 7:
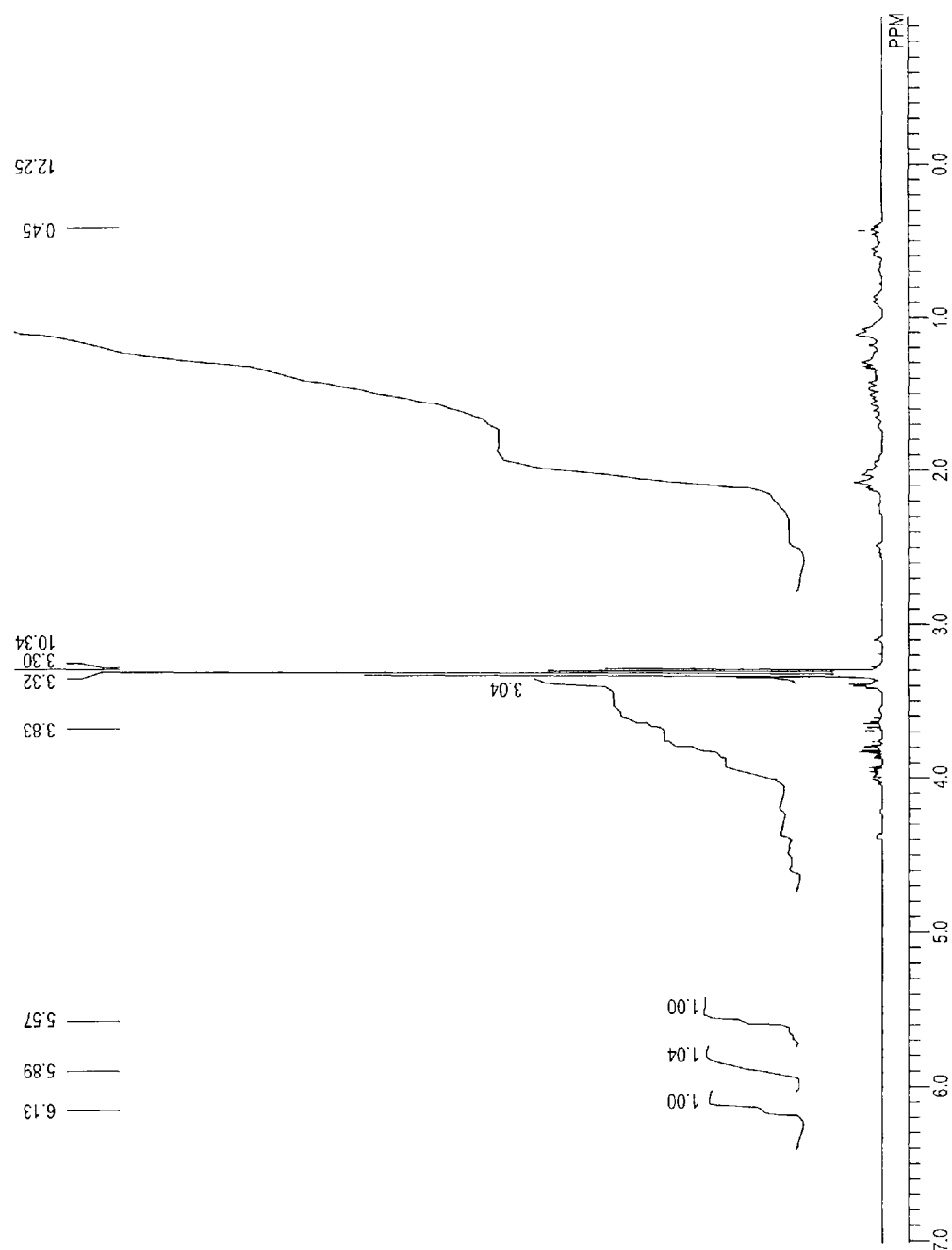
FIG. 7 is a diagram showing the $^1$H NMR spectrum of the reaction product of an example 5.
Figure 8:
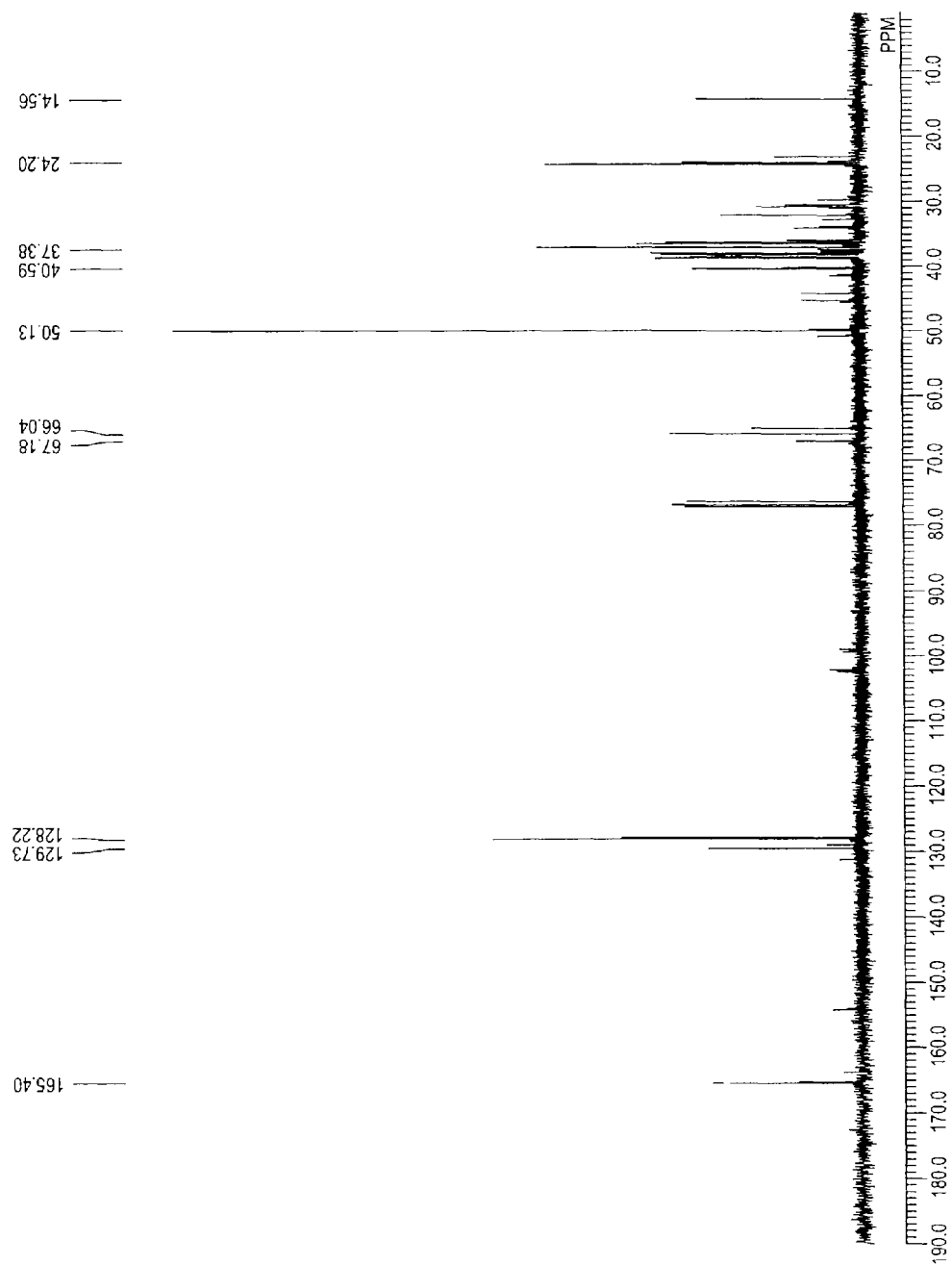
FIG. 8 is a diagram showing the $^{13}$C NMR spectrum of the reaction product of the example 5.
Figure 9:
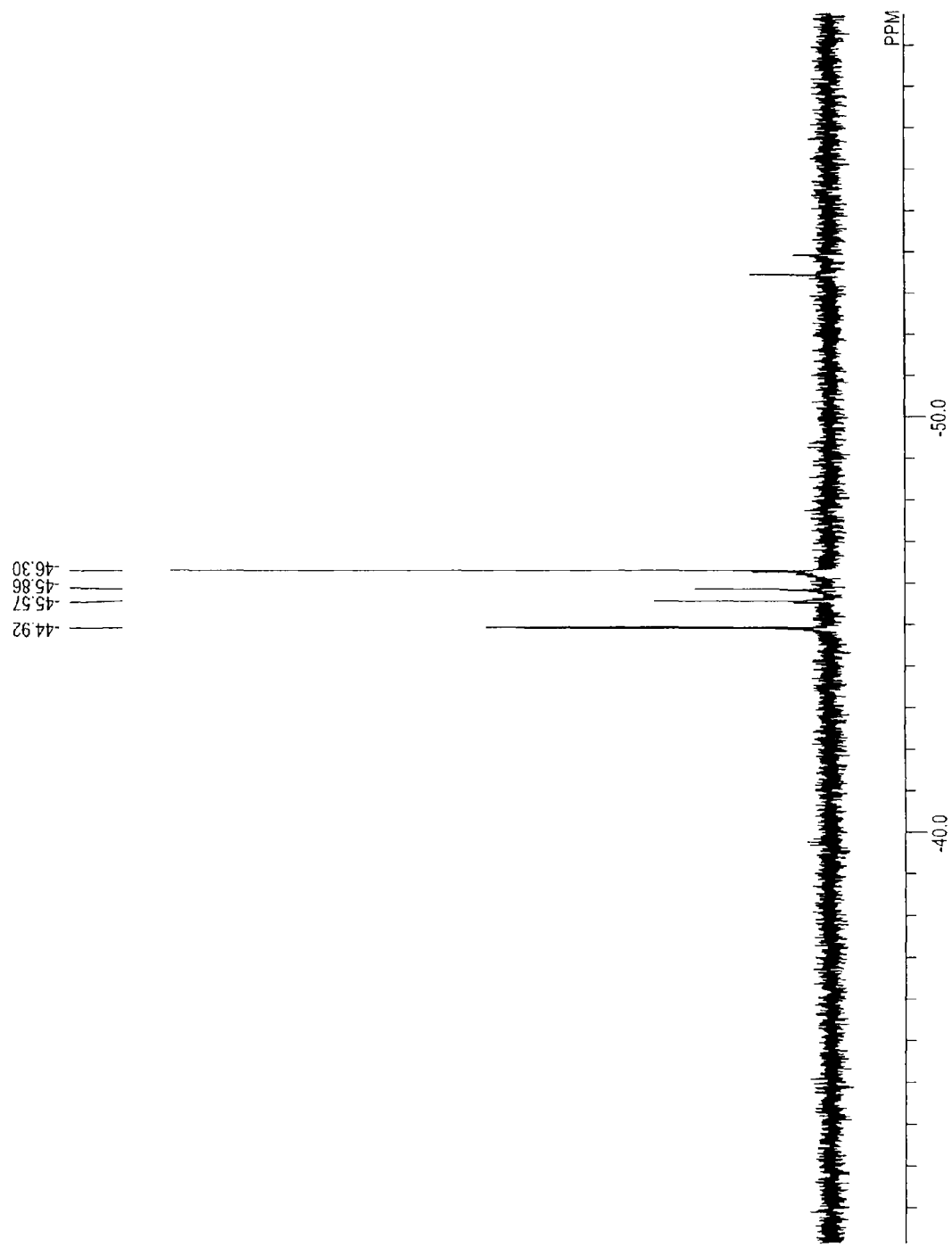
FIG. 9 is a diagram showing the $^{29}$Si NMR spectrum of the reaction product of the example 5.
Figure 10:
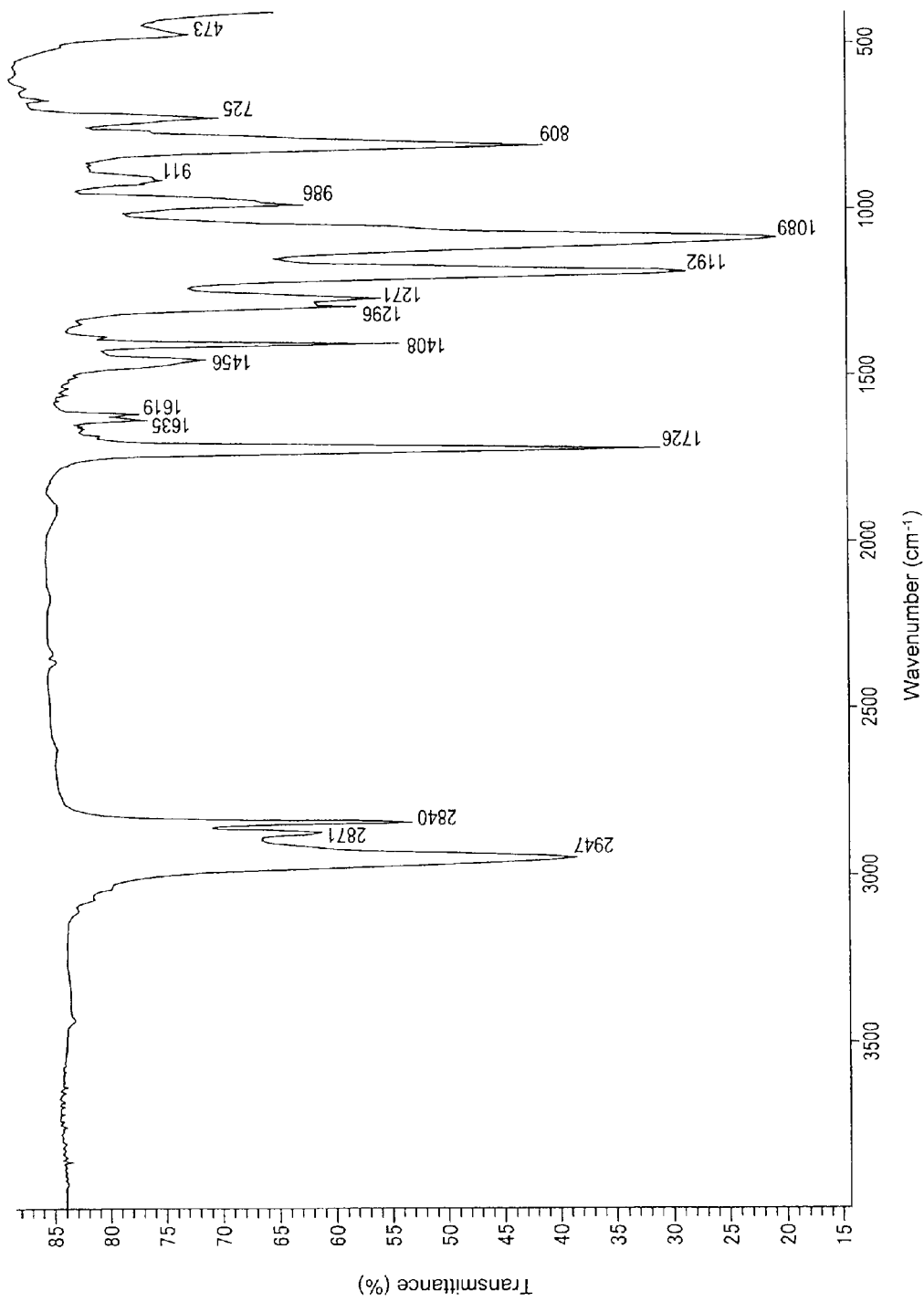
FIG. 10 is a diagram showing the IR spectrum of the reaction product of the example 5.

A 1-liter separable glass flask fitted with a thermometer, a water-cooled condenser and a dropping funnel was charged with 110 g (1.0 mols) of potassium acrylate, 200 g of dimethylformamide, 200 g of toluene and 2.7 g of bis-t-butylhydroxytoluene, the resulting mixture was heated to 140° C., and the water contained within the toluene and potassium acrylate was distilled and removed from the reaction system. Subsequently, the temperature was lowered to 110° C., and 309 g (1.0 mols) of 5-bromomethyl-norbornyltrimethoxysilane was added dropwise to the reaction system. The reaction mixture was then refluxed at 110° C. under constant stirring, while the progress of the reaction was tracked using GC. After 5 hours, GC confirmed that the peak attributable to the raw material methoxysilane had disappeared completely, and a new peak attributable to the reaction product had appeared, and the reaction was halted at this point. Subsequently, the generated potassium bromide was removed by filtration, the reaction solvent was then removed by evaporation under reduced pressure, and the product was then purified by distillation under reduced pressure, yielding a colorless transparent liquid (purified yield: 43%). GC confirmed that the purity of the reaction product was at least 94%. Furthermore, the $^1$H NMR, $^{13}$C NMR, $^{29}$Si NMR and IR spectra confirmed that the reaction product was 5-acryloyloxymethyl-norbornyltrimethoxysilane, was a mixture of endo and exo isomers, and was a mixture of an isomer in which the trimethoxysilyl group was bonded directly to position 2 on the norbornane skeleton structure and an isomer in which the trimethoxysilyl group was bonded directly to position 3 on the norbornane skeleton structure. The NMR spectra of this reaction product are shown in FIG. 7 to FIG. 9, and the IR spectrum is shown in FIG. 10.

$^1$H NMR (300 MHz, CDCl$_3$, δ (ppm)): isomeric mixture 0.43 to 3.22 (m, 12H), 3.32 (s, 9H, Si—OCH$_3$), 5.57 to 6.15 (m, 3H, acrylic group)

$^{13}$C NMR (75 MHz, CDCl$_3$, δ (ppm)): isomeric mixture (main product only listed) 14.6, 24.0, 24.2, 36.7, 37.4, 38.8, 40.6, 50.1 (Si—OCH$_3$), 67.2, 128.2, 129.7, 165.4.

$^{29}$Si NMR (60 MHz, CDCl$_3$, δ (ppm)): isomeric mixture −44.9, −45.6, −45.9, −46.3.

Example 6

With the exception of using 124 g (1.0 mols) of potassium methacrylate instead of the 110 g (1.0 mols) of potassium acrylate used in the example 5, a colorless transparent liquid (purified yield: 35%) was produced in the same manner as the example 5. GC confirmed that the purity of the reaction product was at least 93%. Furthermore, the $^1$H NMR, $^{13}$C NMR, $^{29}$Si NMR and IR spectra confirmed that the reaction product was 5-methacryloyloxymethyl-norbornyltrimethoxysilane, was a mixture of endo and exo isomers, and was a mixture of an isomer in which the trimethoxysilyl group was bonded directly to position 2 on the norbornane skeleton structure and an isomer in which the trimethoxysilyl group was bonded directly to position 3 on the norbornane skeleton structure.

$^1$H NMR (300 MHz, CDCl$_3$, δ (ppm)): isomeric mixture 0.41 to 3.25 (m, 12H), 1.96 (s, 3H), 3.30 (s, 9H, Si—OCH$_3$), 5.55 to 6.10 (m, 2H, methacrylic group)

$^{13}$C NMR (75 MHz, CDCl$_3$, δ (ppm)): isomeric mixture (main product only listed) 14.3, 18.1, 23.8, 24.7, 36.3, 37.4, 38.2, 40.8, 50.9 (Si—OCH$_3$), 66.2, 125.2, 136.7, 167.4.

$^{29}$Si NMR (60 MHz, CDCl$_3$, δ (ppm)): isomeric mixture −44.8, −45.1, −45.7, −46.8.

What is claimed is:

1. A radiation-polymerizable functional group-containing organosilicon compound, comprising:
   (A) a norbornane skeleton structure,
   (B) a hydrolyzable silyl group bonded directly to the norbornane skeleton structure, and
   (C) a radiation-polymerizable functional group bonded to the norbornane skeleton structure, either directly or via a carbon atom, a hetero atom, or a combination thereof,
   wherein the radiation-polymerizable functional group is an acryloyl group, a methacryloyl group, or a combination thereof.

2. The organosilicon compound according to claim 1, represented by a general formula (1) shown below:

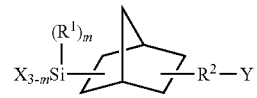

(1)

wherein, each X represents, independently, a halogen atom, an alkoxy group of 1 to 10 carbon atoms, a phenyloxy group, or an acetoxy group,
   Y represents an acryloyloxy group or a methacryloyloxy group,
   R$^1$ represents an alkyl group of 1 to 10 carbon atoms,
   R$^2$ represents an alkylene group of 1 to 10 carbon atoms that either contains, or does not contain, an oxygen atom, a sulfur atom, a nitrogen atom, or a combination thereof, and
   m represents an integer from 0 to 2.

3. The organosilicon compound according to claim 2, represented by a general formula (2) shown below:

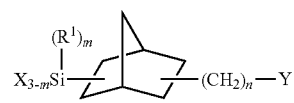

(2)

wherein, X, Y, R$^1$ and m are as defined above, and n represents an integer from 1 to 10.

4. The organosilicon compound according to claim 2, represented by a general formula (3) shown below:

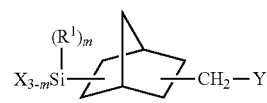

(3)

wherein, X, Y, R$^1$ and m are as defined above.

* * * * *